United States Patent [19]

Di Bella

[11] 4,031,145

[45] June 21, 1977

[54] PROCESS FOR THE PRODUCTION OF 3,4-DICHLOROTOLUENE

[75] Inventor: Eugene P. Di Bella, Piscataway, N.J.

[73] Assignee: Tenneco Chemicals, Inc., Saddle Brook, N.J.

[22] Filed: Mar. 22, 1976

[21] Appl. No.: 669,440

[52] U.S. Cl. .......................................... 260/650 R
[51] Int. Cl.² ....................................... C07C 25/04
[58] Field of Search ................................ 260/650 R

[56] References Cited
UNITED STATES PATENTS 3,000,975  9/1961  Di Bella .................... 260/650 R
3,692,850  9/1972  Di Bella .................... 260/650 R Primary Examiner—D. Horwitz
Attorney, Agent, or Firm—Evelyn Berlow

[57] ABSTRACT

Dichlorotoluene that contains at least 35 percent of 3,4-dichlorotoluene is prepared by contacting para-chlorotoluene with chlorine in the presence of a chlorination catalyst that is either a metal sulfide or a mixture of a ring-chlorination catalyst and a co-catalyst that is a sulfur compound to form a reaction mixture containing para-chlorotoluene, dichlorotoluene, and trichlorotoluene and separating dichlorotoluene from the reaction mixture.

10 Claims, No Drawings

PROCESS FOR THE PRODUCTION OF 3,4-DICHLOROTOLUENE

This invention relates to a process for the production of dichlorotoluenes. More particularly, it relates to a process for the chlorination of para-chlorotoluene whereby there is formed a mixture of dichlorotoluene isomers of unusually high 3,4-dichlorotoluene content.

3,4-Dichlorotoluene is used commercially as a high-boiling solvent and as an intermediate in the production of compounds that are useful as pesticides, lubricants, and dyestuffs. In the past, it has been produced by the diazotization of 3-chloro-4-amino-toluene and the treatment of the resulting intermediate compound with cuprous chloride. It has also produced by the direct chlorinnation of para-chlorotoluene in the presence of iron or another known ring-chlorination catalyst. This process, however, yields a mixture of dichlorotoluenes that contains 77 percent to 82 percent of 2,4-dichlorotoluene and only 18 percent to 23 percent of 3,4-dichlorotoluene. In view of the increasing demand for 3,4-dichlorotoluene, it has become necessary to provide a more effficient process for the production of a dichlorotoluene product that contains a substantially larger amount of 3,4-dichlorotoluene when para-chlorotoluene is chlorinated in the presence of a ring-chlorination catalyst.

In accordance with this invention, it has been found that when para-chlorotoluene is chlorinated in the presence of a catalyst system that comprises a ring-chlorination catalyst and a co-catalyst that is sulfur or a compound containing at least one divalent sulfur atom the dichlorotoluene product that is formed has a 3,4-dichlorotoluene content that is substantially higher than that obtained when the chlorination is carried out in the absence of the co-catalyst.

In the process of this invention, para-chlorotoluene is contacted with chlorine in the presence of a ring-clorination catalyst and a co-catalst as hereinafter defined until the reaction product is a mixture of chlorotoluenes that contains at least 50 percent of dichlorotoluenes. This mixture is then fractionally distilled to separate the dichlorotoluenes from the monochlorotoluene and trichlorotoluenes that are present. The dichlorotoluene fraction, which contains at least 35 percent of 3,4-dichlorotoluene, may be subjected to fractional distillation to yield substantially pure 3,4-dichlorotoluene.

The catalyst systems of this invention may contain any of the ring-chlorination catalysts that are known to be useful in the production of chlorobenzenes and chlorotoluenes. These include, for example, iron, iron chlorides, ferrocene, aluminum chloride, zirconimum tetrachloride, thallium chloride, stannic chloride, indium chloride, molybdenum chloride, gallium chloride, tungsten chloride, iodine, boron trifluoride, and mixtures thereof. The preferred ring-chlorination catalysts are ferrocene, aluminum chloride, and zirconium tetrachloride.

The sulfur compounds that can be used as co-catalysts in the novel catalyst systems include sulfur and a wide variety of organic and inorganic compounds that contain one or more divalent sulfur atoms and that are soluble to at least a limited extent in the reaction mixture. Illustrative of the co-catalysts are sulfur monochloride, sulfur dichloride, carbon disulfide, thiophenes, thiophanes, alkyl-, cycloalkyl-, and aralkyl mercaptans and dimercaptans, thioethers, and the like. The preferred co-catalysts are sulfur monochloride, sulfur, and sulfur-containing compounds that are converted to sulfur monochloride under the conditions of ring-chlorination, for example, sulfur dichloride and carbon disulfide.

In a preferred embodiment of this invention, the combination of ring-chlorination catalyst and co-catalyst is replaced by a metallic sulfide. The useful metal sulfides, which contain at least one divalent sulfur atom, are sulfides of the aforementioned metals whose chlorides are ring-chlorination catalysts. Particularly advantageous results have been obtained when ferrous sulfide was used. The metal sulfide may be added to the reaction mixture as such, or they may be formed in situ by the reaction of the metal chloride that is used as the ring-chlorination catalyst with the sulfur compound that is the co-catalyst.

The catalyst must contain at least 0.1 part by weight of the co-catalyst per part by weight of the ring-chlorination catalyst if the desired high proportion of 3,4-dichlorotoluene is to be obtained. In most cases, 0.5 part to 1.0 part by weight of the co-catalyst is used per part by weight of the ring-chloration catalyst. The use of a larger amount of the co-catalyst does not result in a further increase in the yield of dichlorotoluene or in the 3,4-isomer content of the dichlorotoluene.

The amount of the catalyst system that is used in the process of this invention is that which will produce in good yield a dichlorotoluene fraction that contains at least 35 percent of the 3,4-isomer. At least 0.1 gram of the ring-chlorination catalyst or metal sulfide per mole of para-chlorotoluene is usually required. An amount of the catalyst system that will provide from 0.5 gram to 1.0 gram of the ring-chlorination catalyst or metal sulfide per mole of para-chlorotoluene is generally preferred because it makes possible a reaction rate that is fast enough for commercial operation of the process while inhibiting side-chain chlorination and ring-addition reactions.

The chlorination of para-chlorotoluene is carried out by procedures that are well known in the art. For example, chlorine may be added to a reaction mixture containing para-chlorotoluene and the catalyst system until the increase in the weight of the reaction mixture or in its specific gravity indicates that the desired amount of chlorine has reacted with the para-chlorotoluene. When the chlorination is continued until from about 0.6 gram atom to 0.9 gram atom o chlorine has reacted per mole of para-chlorotoluene, the reaction product contains from about 50 percent to 70 percent by weight of dichlorotoluene, 20 percent to 40 percent by weight of monochlorotoluene, and 2 percent to 15 percent by weight of trichlorotoluene. It preferably contains at least 55 percent by weight of dichlorotoluene and not more than 10 percent by weight of trichlorotoluene. The dichlorotoluene, which may be separated from the monochlorotoluene and trichlorotoluene by fractional distillation or other known technique, contains at least 35 percent and preferably 40 percent or more of 3,4-dichlorotoluene, the remainder being 2,4-dichlorotoluene. The dichlorotoluene isomers may be separated by fractional distillation. The monochlorotoluene fraction may be separated and recycled.

The chloroination of para-chlorotoluene is carried out at temperatures in the range of −20° C. to 70° C,. with 20° C. to 50° C. the preferred range. At temperatures below −20° C., the reaction takes place too slowly to be of commercial interest. At temperatures above 70° C., there is a tendency for side-chain chlorinated reaction by-products to form. Since chlorination is an exothermic reaction, external cooling may be required to maintain the reaction temperature in the desired range.

The rate at which chlorine is added to the reaction mixture does not have an appreciable effect on the yield of dichlorotoluene or on the isomer distribution of the dichlorotoluene product.

The invention is further illustrated by the following examples.

EXAMPLES 1–4

A series o ring-chlorinations of para-chlorotoluene was carried out in the presence of various catalyst systems according to the following general procedure:

A mixture of 253 grams (2.0 moles) of para-chlorotoluene and a catalyst system in a glass chlorination vessel was chlorinated by passing a stream of chlorine over its surface at the rate of about 60 grams per hour until from 100 to 107 grams of chlorine (0.70–0.75 mole of $Cl_2$ per mole of p-chlorotoluene) had been added. During the chlorination, the reaction mixture was stirred, and its temperature was maintained at 34°–36° C. by external cooling. Samples of the chlorination mixture were analyzed by gas-liquid chromatography. The catalyst systems used and the results obtained are summarized in the Table.

COMPARATIVE EXAMPLES A–D

For comparative purposes, a series of chlorinations of para-chlorotoluene using known ring-chlorination catalysts was carried out by the procedure described above. The catalysts used and the results obtained are summarized in the Table.

monochloride, the ratio of the 3,4-isomer to the 2,4-isomer is 43.7/56.3 or 0.82/1.

What is claimed is:

1. The process for the production of dichlorotoluene containing at least 35 percent of 3,4-dichlorotoluene which comprises contacting para-chlorotoluene with chlorine until from about 0.6 gram atom to 0.9 gram atom of chlorine has reacted per mole of para-chlorotoluene in the presence of a catalyst system selected from the group consisting of
   a. a ring-chlorination catalyst selected from the group consisting of iron, ferrocene, chlorides of iron, aluminum, zirconium, thallium, tin, indium, molybdenum, gallium, tungsten and mixtures thereof and a co-catalyst selected from the group consisting of sulfur, sulfur monochloride, sulfur dichloride, and carbon disulfide in the amount of at least 0.1 part by weight of the co-catalyst per part by weight of the ring-chlorination catalyst;
   b. a sulfide of a metal selected from the group consisting of iron, aluminum, zirconium, thallium, tin, indium, molybdenum, gallium, tungsten, and mixtures thereof; and
   c. mixtures thereof, in the amount of at least 0.1 gram of the ring-chlorination catalyst or metal sulfide per mole of parachlorotoluene and at a temperature in the range of −20° C. to 70° C. to form a reaction mixture that contains from 50 percent to 70 percent by weight of dichlorotoluene and separating from said reaction mixture a dichlorotoluene fraction containing at least 35 percent of 3,4-dichlorotoluene.

2. The process of claim 1 wherein the catalyst system comprises a ring-chlorination catalyst selected from the group consisting of iron, ferrocene, chlorides of iron, aluminum, zirconium, thallium, tin, indium, molybde-

TABLE

| Ex. No. | Catalyst System | Amount of Catalyst (g. per mole of p-Cl toluene) | Chlorine Charged (moles $Cl_2$ per mole p-Cl toluene) | Chlorination Level (gram atoms Cl substituted per mole p-Cl toluene) | Product Composition (% by wt.)* | | | Isomer Distribution in Dichlorotoluene (%) | |
|---|---|---|---|---|---|---|---|---|---|
| | | | | | Monochlorotoluene | Dichlorotoluene | Trichlorotoluene | 2,4- | 3,4- |
| 1 | Ferrocene $S_2Cl_2$ | 1.0 0.5 | 0.70 | 0.67 | 33.8 | 56.7 | 9.5 | 60.0 | 40.0 |
| 2 | $AlCl_3$ $S_2Cl_2$ | 1.0 1.0 | 0.73 | 0.73 | 29.3 | 60.1 | 10.6 | 60.9 | 39.1 |
| 3 | $ZrCl_4$ $S_2Cl_2$ | 1.0 1.0 | 0.75 | 0.75 | 29.1 | 58.5 | 12.4 | 56.3 | 43.7 |
| 4 | FeS | 1.0 | 0.72 | 0.71 | 31.5 | 57.5 | 11.0 | 59.7 | 40.3 |
| Comparative Examples | | | | | | | | | |
| A | Ferrocene | 1.0 | 0.72 | 0.45 | 50.4 | 46.6 | 3.0 | 76.7 | 23.2 |
| B | Fe | 0.5 | 0.72 | 0.71 | 29.2 | 62.1 | 7.8 | 77.5 | 22.5 |
| C | $AlCl_3$ | 1.0 | 0.72 | 0.71 | 30.6 | 59.7 | 9.7 | 77.1 | 22.9 |
| D | $ZrCl_4$ | 1.0 | 0.74 | 0.73 | 25.8 | 68.8 | 5.4 | 81.8 | 18.2 |

*The gas-liquid chromatography data have been normalized to exclude the <0.5% of volatile materials added with the catalyst components.

From the data in the Table, it will be seen that when a catalyst system that comprises either a metal sulfide or a ring-chlorination catalyst and a sulfur co-catalyst is used in the chlorination of para-chlorotoluene, there is a sizeable increase in the 3,4-dichlorotoluene content of the dichlorotoluene fraction over that obtained when only a ring-chlorination catalyst is used. This shift in the ratio of the 2,4-isomer to the 3,4-isomer is most pronounced when the ring-chlorination catalyst is zirconium tetrachloride. When the catalyst is zirconium tetrachloride, the ratio of the 3,4-isomer to the 2,4-isomer is 18.2/81.8 or 0.22/1, whereas when the catalyst system consists of zirconium tetrachloride and sulfur num, gallium, tungsten, and mixtures thereof and a co-catalyst selected from the group consisting of sulfur, sulfur monochloride, sulfur dichloride, and carbon disulfide in the amount of 0.5 part to 1.0 part by weight of the co-catalyst per part by weight of the ring-chlorination catalyst.

3. The process of claim 2 wherein the ring-chlorination catalyst is ferrocene.

4. The process of claim 2 wherein the ring-chlorination catalyst is aluminum chloride.

5. The process of claim 2 wherein the ring-chlorination catalyst is zirconium tetrachloride.

6. The process of claim 2 wherein the co-catalyst is sulfur monochloride.

7. The process of claim 1 wherein the catalyst system comprises ferrous sulfide.

8. The process of claim 1 wherein the amount of the catalyst system that is used in that which will provide from 0.5 gram to 1.0 gram of the ring-chlorination catalyst or metal sulfide per mole of para-chlorotoluene.

9. The process of claim 1 wherein the chlorination is carried out at a temperature in the range of 20° C. to 50° C.

10. The process of claim 1 wherein the dichlorotoluene fraction is fractionally distilled to yield substantially pure 3,4-dichlorotoluene.

* * * * *

UNITED STATES PATENT AND TRADEMARK OFFICE
CERTIFICATE OF CORRECTION

PATENT NO. : 4,031,145
DATED : June 21, 1977
INVENTOR(S) : Eugene P. DiBella

It is certified that error appears in the above-identified patent and that said Letters Patent are hereby corrected as shown below:

Column 1, line 17, change "chlorinnation" to -- chlorination --.

Column 1, line 39, change "ring-clori" to -- ring-chlori --.

Column 1, line 40, change "co-catalst" to -- co-catalyst --.

Column 1, line 54, change "zirconimum" to -- zirconium --.

Column 2, line 49, change "o" to -- of --.

Column 2, line 65, change "chloroination" to --chlorination --.

Column 3, line 15, change "o" to -- of --.

Signed and Sealed this

Twenty-seventh Day of September 1977

[SEAL]

Attest:

RUTH C. MASON
Attesting Officer

LUTRELLE F. PARKER
Acting Commissioner of Patents and Trademarks